US006254583B1

(12) United States Patent
Coates

(10) Patent No.: US 6,254,583 B1
(45) Date of Patent: Jul. 3, 2001

(54) REUSABLE AND PROTECTIVE UNDERWEAR HAVING IMPROVED CONTAINMENT PROPERTIES AND IMPROVED FIT AND CONSTRUCTION METHODS THEREOF

(75) Inventor: Fredrica V. Coates, Earlysville, VA (US)

(73) Assignee: Tailored Technologies, Inc., Earlysville, VA (US)

( * ) Notice: Subject to any disclaimer, the term of this patent is extended or adjusted under 35 U.S.C. 154(b) by 0 days.

(21) Appl. No.: 08/792,735

(22) Filed: Jan. 31, 1997

(51) Int. Cl.[7] ............................................ A61F 13/15

(52) U.S. Cl. .................. 604/385.14; 604/385.19; 604/385.26; 604/385.28; 604/385.29; 604/398; 604/394; 604/401; 604/402; 604/391

(58) Field of Search .................. 604/373, 385.1, 604/385.2, 386, 391, 393–402, 385.14, 385.19, 385.24, 385.3

(56) References Cited

U.S. PATENT DOCUMENTS

| 5,707,364 | * | 1/1998 | Coates | 604/385.1 |
| 5,725,518 | * | 3/1998 | Coates | 604/391 |
| 5,814,037 | * | 9/1998 | Coates | 604/385.1 |
| 5,891,122 | * | 4/1999 | Coates | 604/385.1 |

* cited by examiner

Primary Examiner—Aaron J. Lewis
Assistant Examiner—K. M. Reichle
(74) Attorney, Agent, or Firm—McDermott, Will & Emery

(57) ABSTRACT

A protective undergarment having an outer shell of fluid resistant material and a fluid containment sling of fluid resistant material connected to the inner surface of the shell and adapted to receive and retain a fluid absorbent pad. The ends of the shell are folded in to establish frontal and rear bumpers. One end of the sling is folded under the frontal bumper to form a pocket that is attached to and hidden beneath the frontal bumper, and remains open to receive one end of the fluid absorbent pad. The other end of the sling is attached to the rear bumper. This construction accommodates a pad of greater length for improved absorption without increasing the length of the shell. Methods of constructing protective undergarments with unique hidden pocket slings and fasteners are described.

17 Claims, 7 Drawing Sheets

REUSABLE AND PROTECTIVE UNDERWEAR HAVING IMPROVED CONTAINMENT PROPERTIES AND IMPROVED FIT AND CONSTRUCTION METHODS THEREOF

TECHNICAL FIELD

This invention relates generally to protective underwear for all age groups from newborns through geriatric, and more particularly to improvements for collection of body fluids and fecal matter. The invention further relates to novel protective underwear construction methods that reduce manufacturing costs and improve fit.

BACKGROUND ART

To enhance protective underwear for collection of fluid and fecal matter, protective underwear in the form of a diaper outer shell containing an inner waterproof or water resistant "sling" positioned within the shell to cover a user's groin when the diaper is worn was previously developed. Within the sling is a fluid absorbent pad that may be removable. A fluid-resistant sling, with its connecting pieces adjoined to an outer shell, was first disclosed in U.S. Pat. Nos. 5,137,526 and 5,409,976. This fluid-resistant sling isolates body fluids from spreading to or beyond the outer shell region of the undergarment by the use of elastic on the outer edge of the shell or waterproof gussets mounted on opposite sides of the inner attached pad. The sling has a waterproof undersurface floating inside the outer shell. These various types of slings have proved satisfactory, although containment of fluid remains limited.

In subsequent work, the sling is improved to form a deeper pocket, and unique fasteners applied to retain the garment to the user with improved fit and, in the case of an infant user, the garment can "grow" as the infant grows. Because a baby can be on a total fluid diet for several months and conditions such as teething can produce loose stools, even with improved fit and deeper inner pocketed slings, there still remains a need for a greater area for containment of fluid and fecal matter. This is true especially for smaller infants who produce large quantities of fluid relative to the size of their small bodies.

Protective underwear constructions that attempt to increase fluid absorption may tend to be bulky and bunching may be visible from outside of clothing because not enough space is provided in the garment for absorbing material. In addition, manufacturing costs must be minimized to enable the product to have appeal to a broad market.

DISCLOSURE OF THE INVENTION

One advantage of this invention is in improving the containment properties of protective underwear including pants for adults and diapers for infants.

Another advantage of the invention is in improved diaper underwear that is capable of accommodating infant growth as well as providing space to help in healing of their umbilicus.

Another advantage is in maximizing the size of a diaper sling and pad for greater absorbency while retaining good external appearance or the user.

A further advantage is in preventing migration of fluid to the outside of protective underwear.

An additional advantage is in reducing manufacturing costs while realizing performance and fit improvements to protective underwear as disclosed herein.

In accord with one aspect of the invention, A method of manufacturing a protective undergarment, comprises the steps of:

patterning one end of a generally rectangular piece of fluid resistant material to have a central projecting region adjoining sides demarked by a pair of notches cut into the material to form a sling;

backfolding the projecting region against said notches and folding in the sides of the sling;

securing the backfolded region of the sling to a frontal portion of a diaper shell;

folding the frontal portion of the shell, together with said backfolded sling region, onto an inner surface of the shell to form, at the same time, a shell frontal bumper and a hidden sling pocket;

stitching front ends of the sides of the sling and sides of the pocket to an undersurface of the frontal bumper while leaving a front end of the pocket open as the access opening to the pocket;

folding a rear portion of the shell to form a rear bumper; and stitching said rear bumper to a rear edge of the sling.

Another aspect of the invention provides a protective undergarment, comprising:

an outer shell formed of fluid resistant material and having frontal and rear ends folded in to an inner surface of said shell to form frontal and rear bumpers; and a sling formed of a fluid resistant material and having frontal and rear ends connected respectively to the frontal and rear bumpers, opposite sides of the frontal end of the sling being folded toward each other and connected to said frontal bumper, said frontal end of said sling having a central projecting portion extending beneath said frontal bumper, and said central projecting portion having three sides attached and a fourth side unattached to an inner surface of said frontal bumper for forming a hidden pocket with an opening at the unattached side of the central projecting portion to receive one end of a fluid absorbent pad.

A further aspect of the invention provides a protective undergarment, comprising:

an outer shell formed of fluid resistant material;

frontal and rear end portions of the outer shell folded to an inner surface of the outer shell to form frontal and rear connecting pieces of fluid resistant material; and a sling formed of a rectangular piece of fluid resistant material having a central projecting portion of material demarked by a pair of notches cut into the sling defining opposite sides of said sling which fold laterally inward and attach to said one of said frontal and rear connecting pieces, the central projecting piece having three sides attached and a fourth side unattached to an inner surface of said one of said frontal and rear connecting pieces and forming a hidden pocket with an opening at the unattached side of the central projecting piece to receive one end of a fluid absorbent pad.

In one embodiment, fastener strips project from the sides of the rear portion of the shell to couple to a complementary filamentary fastener strip on the frontal portion of the outside of the shell. The projecting fastener strips are improved by stitching one end of a fastening strip to the garment before the bumper is folded over it. Once attached, the bumper is folded over and secures the strip to the shell. Additionally, a second complementary strip is attached to the rear bumper and folds in adjacent the projecting strip and also overlies the ends of the elastic trim.

The fastening strips may comprise filamentary fastener material. Snap fasteners can replace filamentary type fasteners and be applied for security within the frontal and rear folding mechanisms, for additional security and comfort when the undergarment is worn.

Still other objects and advantages of the present invention will become readily apparent to those skilled in the art from which the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BEST MODE FOR CARRYING OUT THE INVENTION

Figure 1:
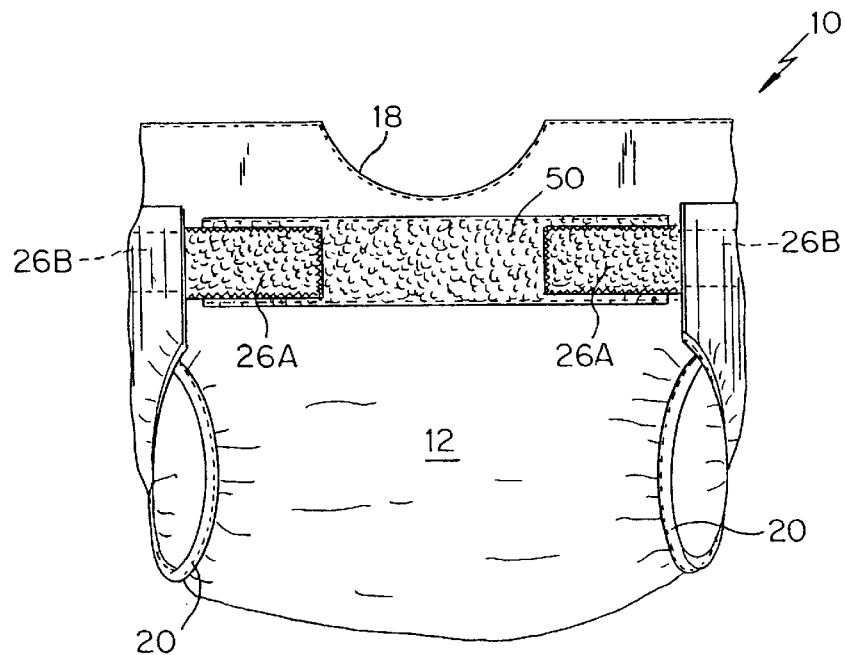
FIG. 1 is a front view, with portions deleted for clarity, of a newborn reusable diaper within which the principles of the present invention are implemented.
Figure 1A:
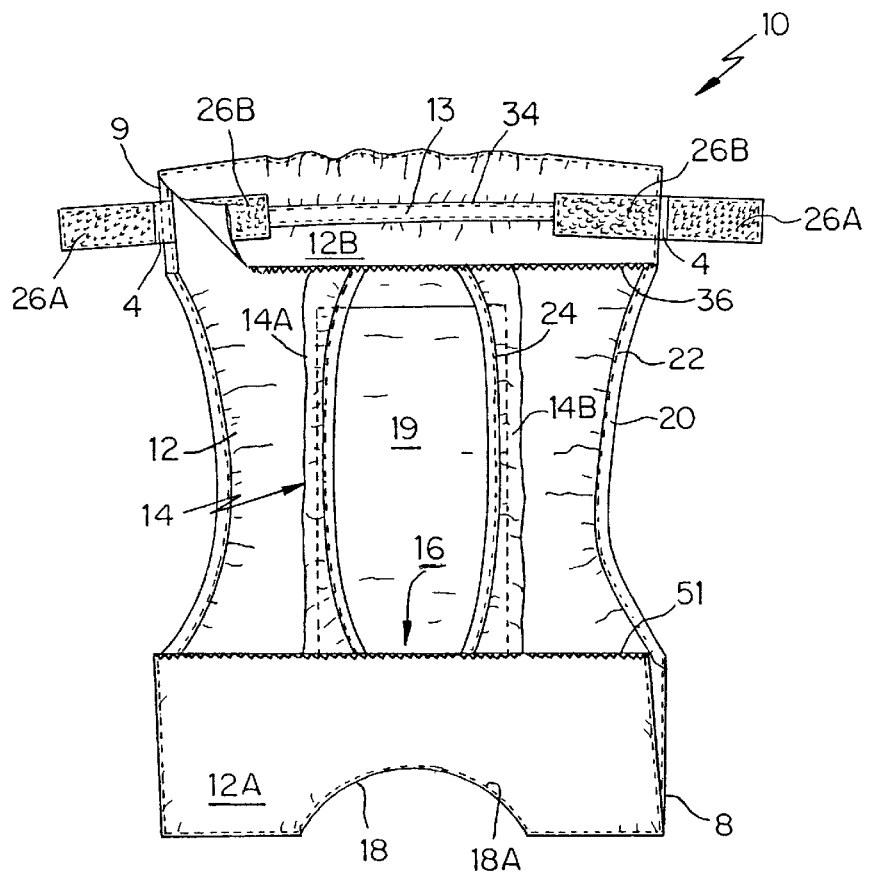
FIG. 1A is a view of the inside of the reusable diaper, with portions deleted for clarity, in accordance with the invention.
Figure 2:
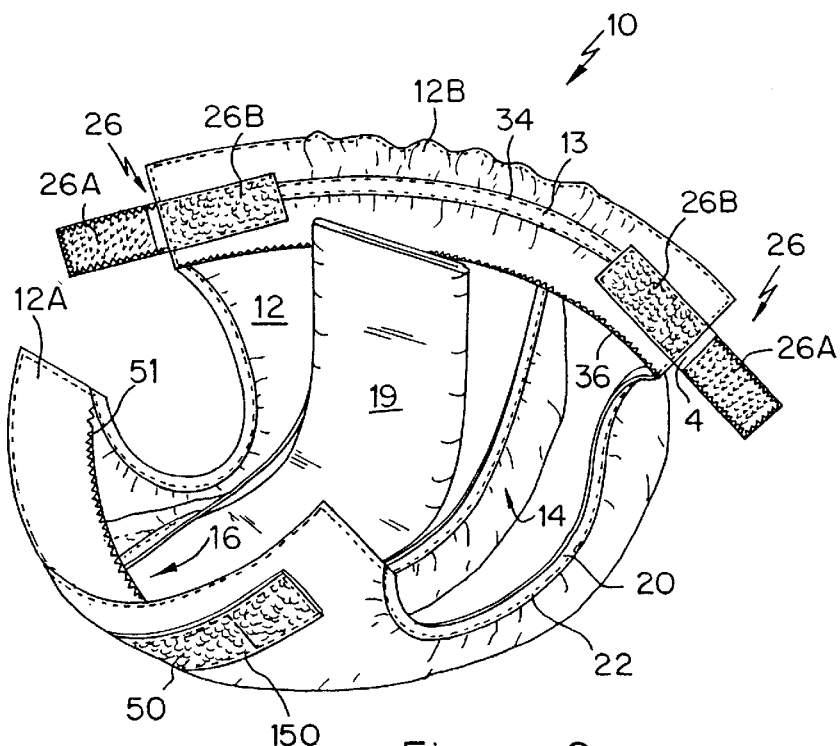
FIG. 2 is a perspective view, with portions deleted for clarity, of another diaper implementing the invention.
Figure 2A:
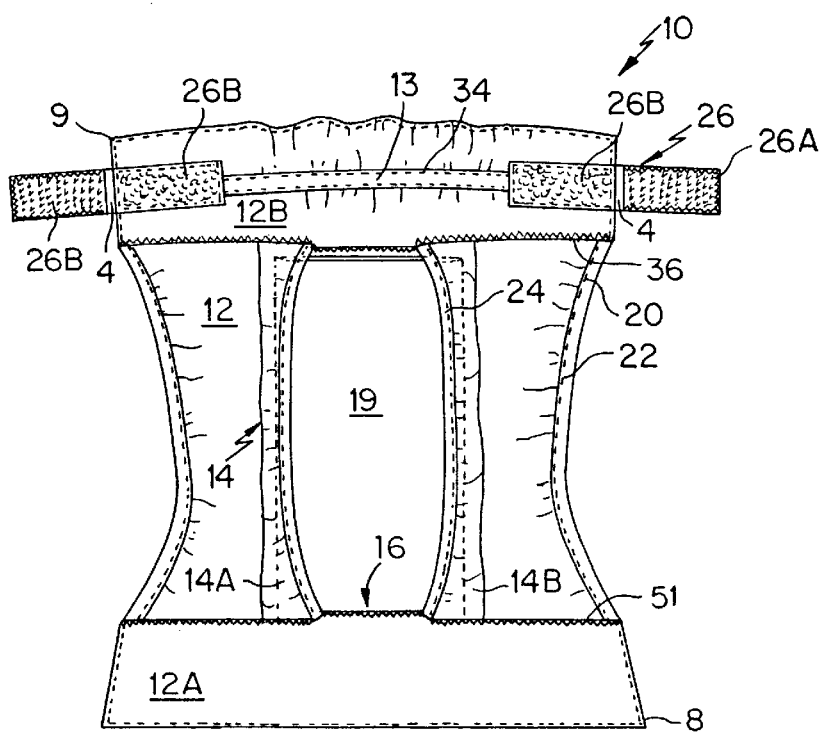
FIG. 2A is a plan view, with portions deleted for clarity, of the diaper of FIG. 2 with interior exposed and pad inserted.

Referring to FIGS. 1, 1A, 2 and 2A, and initially to FIG. 1, depicted is protective underwear, for example, a diaper 10, comprising a diaper shell 12 of fluid resistant, or waterproof material, LYCRA material or other like material, and a pair of fastening tabs 26A extending from the rear portion of the diaper shell onto a frontal fastening strip 50 on the outer surface of the shell. The fastening tabs and strip 26A, 50, are depicted in this example as comprising filamentary fastening material. The frontal outer portion of diaper shell 12 has an optional semi-circular cut-out 18 providing space for the umbilicus of newborn babies to heal by allowing air to contact without irritation by fabric. An inner attached fluid resistant sling 14, shown in FIGS. 1A, 2 and 2A, retains a removable absorbent reusable pad 19. Diaper 10 has a novel "hidden pocket" 16 of a construction in accordance with the invention that enables the length of the absorbent pad 19 to be greater than heretofore possible in the sling-type diapers described in U.S. Pat. Nos. 5,137,526 and 5,409,976, incorporated herein by reference. FIGS. 2 and 2A omit the optional cut-out 18.

Referring now to FIG. 1A in more detail, the diaper shell 12 has a frontal outer portion of material folded inward at region 8, and a rear outer portion of material folded inward at region 9. The frontal folded region becomes an inner connecting piece of a fluid resistant material, termed an "inner bumper" 12A. The rear folded region becomes a inner connecting piece of fluid resistant material, a "rear bumper" 12B. Within the diaper shell 12 and attached to bumpers 12A and 12B, is the fluid containment sling 14 which is positioned to locate pad 19 about the groin when the diaper is worn.

Advantageous containment properties of pocketed sling 14 are established with the integral sides 14A and 14B of the sling projecting away from the surface of the shell and folded toward the groin. The sides of 14A and 14B of sling 14 are covered by an elastic trim 24 that helps retain the inserted pad 19 against the infant's groin.

Sling 14 has an extended rectangular projection of material 32 (see FIGS. 3A–3G) which is inserted under and attached directly beneath folded frontal bumper 12A. The first attachment occurs where this inserted hidden material or projection 32 is caught in stitching 18A surrounding the cut-out 18. Once the terminal end of sling 14 is stabilized by stitching 18A, projection 32 becomes a novel "hidden pocket" 16 as stitching line 150 (see FIGS. 3A–3G) partially circumscribes it in a stitched pattern which further secures the fabric projection 32 between outer shell 12 and connecting frontal bumper 12A. The sides of stitching 150 are spaced apart enough to allow room for pad 19 to be inserted in hidden pocket 16. The pad 19 is more centrally held in place and secured by the folded sides 14A and 14B of sling 14. To attach sides 14A and 14B in the frontal region of the shell, the frontal outer perimeter edge of frontal bumper 12A is attached with overlock stitch 51 to sling 14 at between matching fabric cut notches to be described later with reference to FIG. 3A in the shell so that the folded in sides 14A and 14B are attached to the bumper 12A. The rear perimeter edge of bumper 12B joins with the folded-in edges of sling sides 14A and 14B at additional shell notches (see FIGS. 3A–3G) and sewn together by overlock stitch 36. Sling 14 and sides 14A and 14B overlie each other and are sewn to the rear bumper 12B, in a method of attachment used in the prior patents cited earlier. Construction details will be described later herein.

In the embodiment of FIGS. 2 and 2A, differing from that of FIG. 1 in that cut-out 18 is omitted and the hidden pocket 16 is constructed slightly differently, the diaper shell 12 is generally hourglass in shape with rectangular folded ends. The opposite sides of the hourglass are gathered by trim 20 at stitch line 22 to accommodate the thighs of the user. At the rear portion of the diaper 10, projecting from opposite corners is a pair of fastener strips 26 comprising hook-type filamentary material 26A mounted to the back of a strip of loop-type filamentary material, one end of 26A being bare of hook and forming a hinge 4 that is attached to the shell. The hook-type filamentary material strip 26A couples with loop-type filamentary fastener strip 50 on the outside surface of the frontal region of the diaper shell when the diaper is worn. As the infant grows, the fasteners 26A will be more widely spaced apart from each other on loop-type fastener 50. In this manner, the diaper "grows" with the infant.

Adjacent the hook-type strip 26A and spaced slightly therefrom on the folded rear bumper 12B portion of the shell 12 is a strip 26B of loop-type filamentary material. The region between the hook- and loop-type strips 26A and 26B forms a hinge 4 about which the hook strip 26A will tend to pivot during washing and couple to the loop-type strip 26B for protection from lint accumulation. On the rear bumper 12B of the diaper shell 12 is stitched a strip of elastic trim material 13 that extends between loop-type fastener strips 26B. The trim 13 is stitched and gathers the folded rear bumper 12B to outer shell 12 at stitch line 34, and conforms the shell to the buttocks region of the infant. Hidden frontal pocket 16 is formed at stitch line 150 (see FIGS. 3A–3G) that pierces and connects shell 12 to bumper 12A. The projected material 32 of sling 14 is now sealed between bumper 12A and the shell 12 by stitch line 150.

Beneath the frontal bumper 12A of the shell 12 and integral with the sling 14, is the novel hidden sling pocket 16 that is open to receive one end of pad 19. As in the embodiment of FIGS. 1 and 1A, the hidden pocket 16 in effect increases the length of the sling 14 and enables retention of a longer pad 19 than otherwise possible if the sling had terminated at the interface between the bumper and shell as in the prior art. Referring to FIGS. 3A–3G, stitch lines 150 form hidden pocket 16 as stitch line 33 stabilizes the end of the sling fabric at the projected material 32 and together with stitch line 150 establishes and stabilize the sides of the pocket. The rest of the construction of the sling is the same as described with respect to FIG. 1A.

Figure 3A:
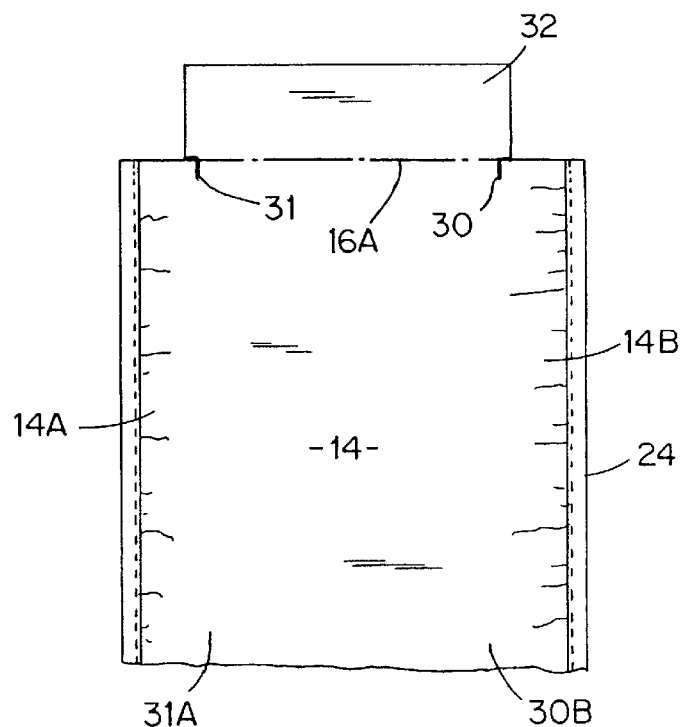
FIGS. 3A–3G depict a method of manufacturing the diaper with hidden pocket, in accordance with the invention.

Manufacturing of the diaper heretofore described, with hidden pocket 16 of FIGS. 2, 2A, is shown in FIGS. 3A–3G. In FIG. 3A, the sling 14 of the fluid resistant material initially is patterned as shown with a central region at the frontal end of the sling material projecting at 32, and the adjoining sides 14A and 14B of sling 14 are notched at 31, 30. Similar cut notches 31A, 30B are made at the rear end of the sling 14, and again demark the sides 14A and 14B respectively. The projection 32 will later serve to anchor the hidden pocket 16, not shown in FIG. 3A. The sides 14A and 14B of the sling material are covered by elastic trim 24 through stitch lines.

Figure 3B:
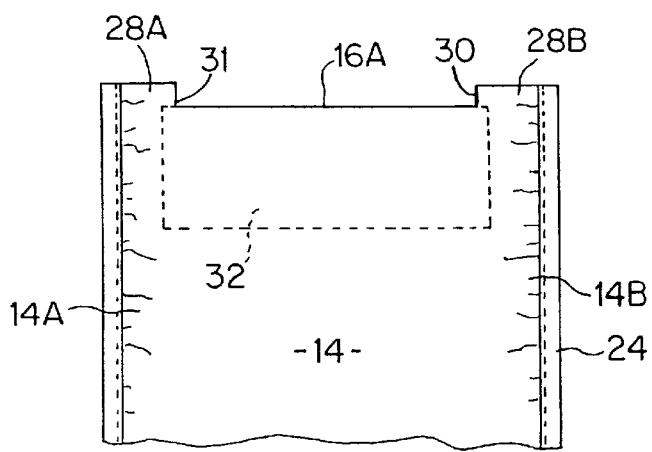

In FIG. 3B, the projection 32 is folded backward at fold line 16A and cut notches 31 and 30 of sling 14. The remaining material 28A and 28B not folded down become temporary extensions of the sides 14A and 14D of the sling.

Figure 3C:
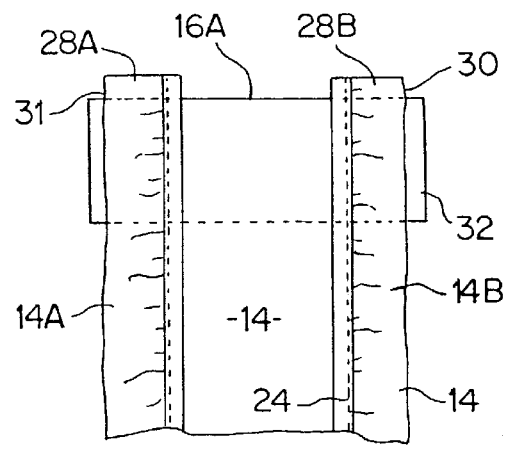

In FIG. 3C, the sling sides 14A and 14D are folded inward as they pivot about cut notches 31, 31A and 30, 30B (only notches 31, 30 are shown in FIG. 3C).

Figure 3D:
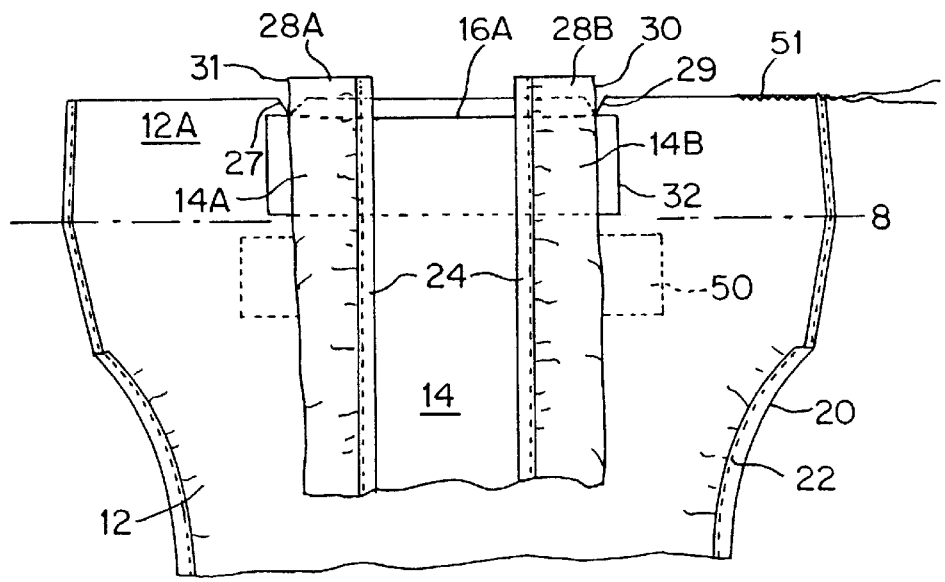

In FIG. 3D, the frontal projection 32, previously folded backward at 16A onto the backside of sling 14 in a previous step, is positioned between the underside of bumper 12A and the backside of sling 14. The sling 14 is now joined to bumper 12A by an overlock stich sewing operation at 51 which aligns shell 12 so that the notches 27, 29 on the shell 12 match the cut notches 31, 30 of sling 14. Temporary extensions 28A and 28B are then removed during the sewing operation whereby the overlock stitch sewing operation cuts and joins the sling sides 14A, 14B to connecting frontal bumper 12A.

Figure 3E:
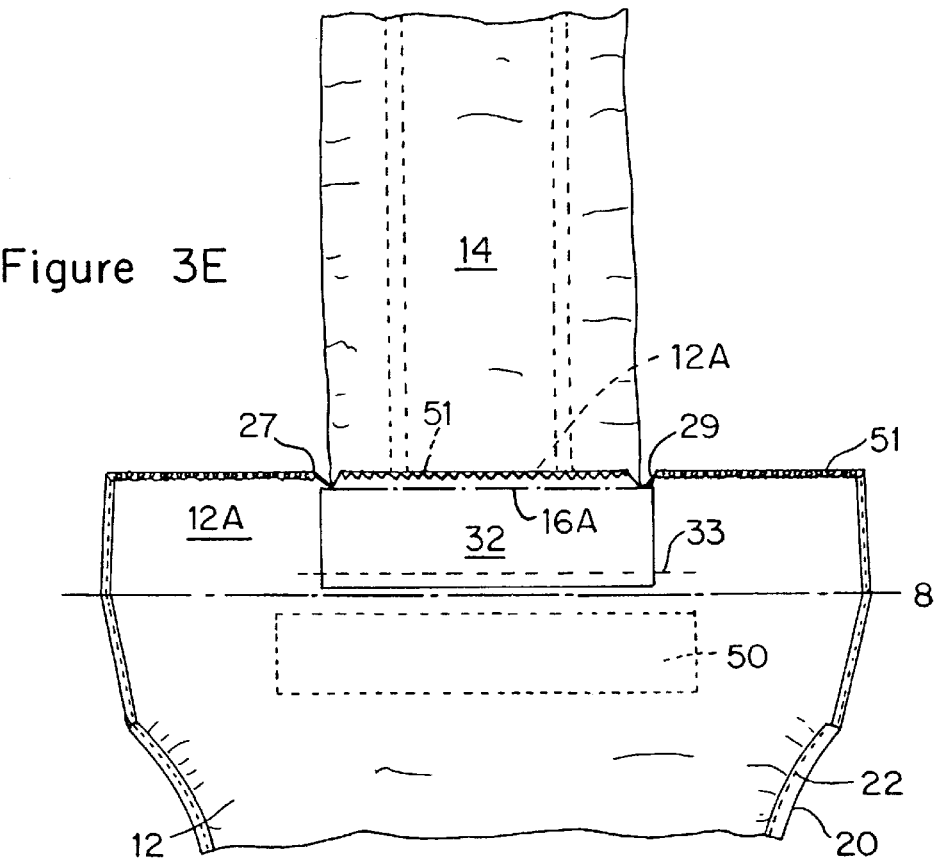

In FIG. 3E, the joined sling 14 and its projection 32 are next stitched to the shell 12 at stitch line 33 to stabilize the sling to the underside of the frontal bumper 12A. With the sling 14 attached and extending outwardly from the inner surface of shell 12 as in FIG. 3E, the frontal bumper 12A is folded inward at fold line 8, establishing the frontal bumper 12A and resting the sling 14 on the inner surface of the shell, shown in FIG. 3F.

Figure 3F:
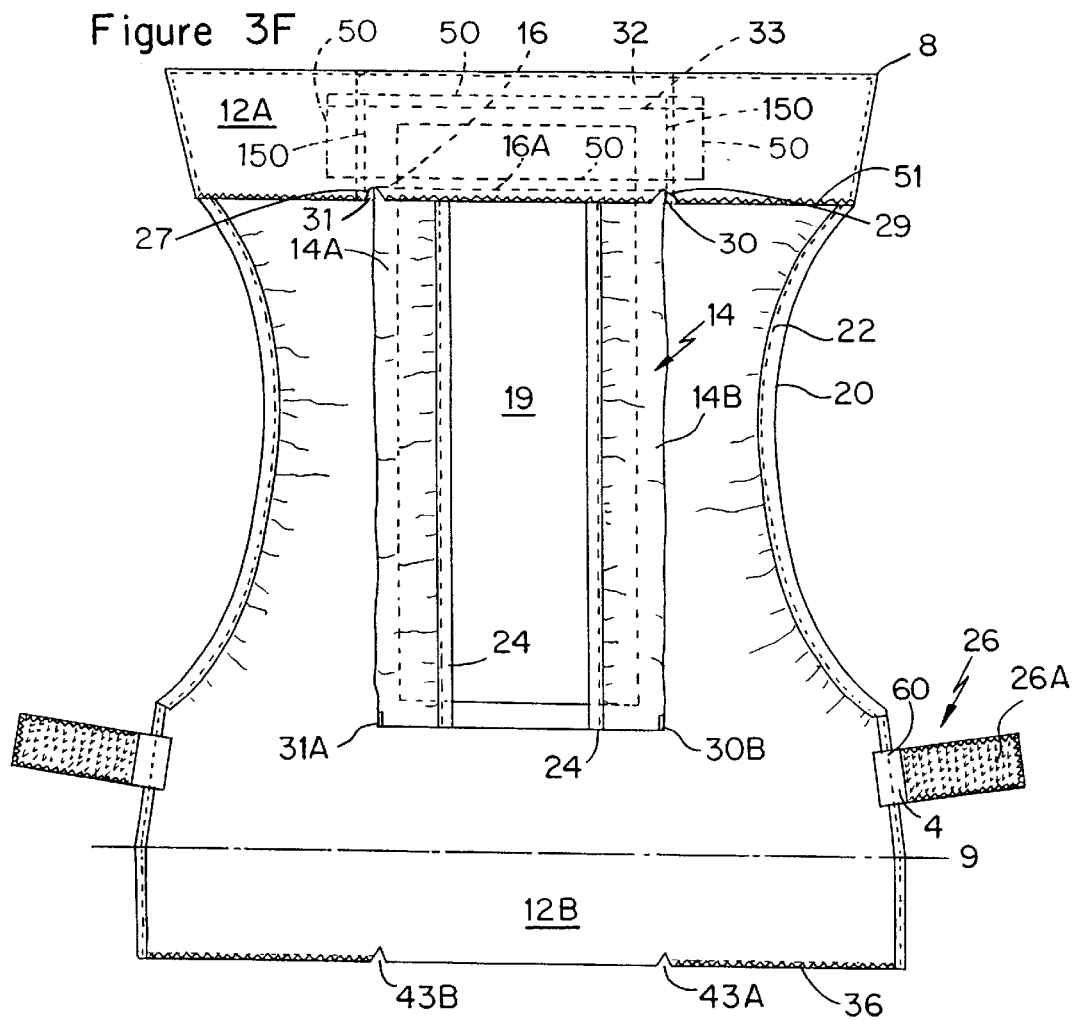

In FIG. 3F, with the sling 14 now resting on shell 12 and attached to frontal bumper 12A, and with sides 14A and 14B having been stabilized inward by stitching 51, there still remains an open space between the bumper 12A and projected material 32 sewn at 33 because only the side portions 14A and 14B have been attached to bumper 12A. Another stitch 150 penetrates the frontal bumper 12A to partly circumscribe and further retain the loop-type fastener strip 50 to the outer surface of the shell and the pocket 16 on the inner side of the shell while the pocket 16 is formed in the inner side of the shell. Stitching 150 is displaced from each end of the strip 50 on the inner side of shell. This process simultaneously finishes encasing projection material 32 between bumper 12A and shell 12. The spacing between stitches of the stitching pattern 150 is great enough to receive and retain a pad 19, as shown.

Still referring to FIG. 3F, fastener strips 26A are stitched to the sides of the shell near the rear portions of the leg openings and their trims 20. The 12B bumper of the shell 12 is folded inward at line 9 to cover and secure the fastener strips 26A on hinge 4.

Figure 3G:
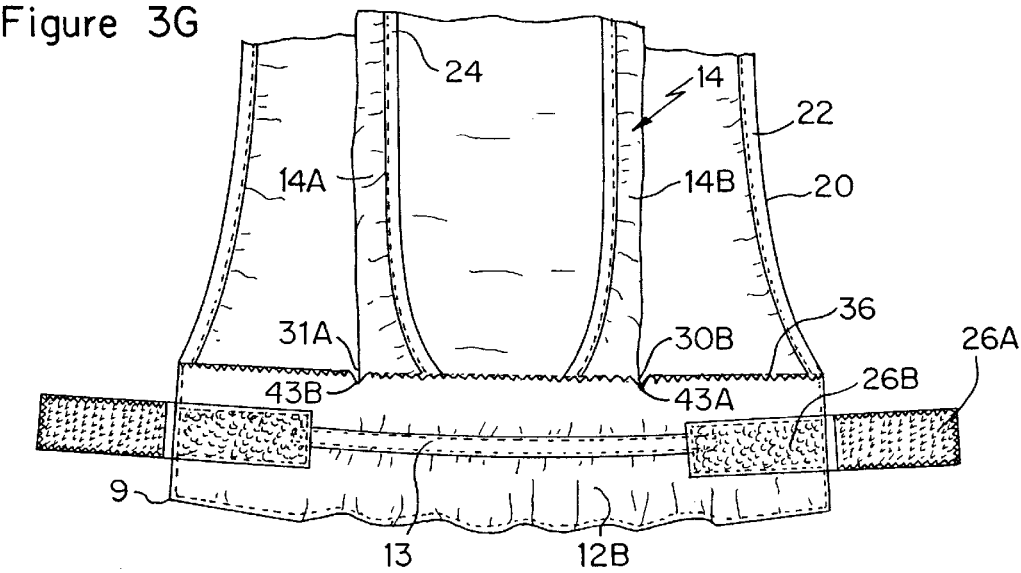

In FIG. 3F, the cut notches 43A and 43B of the rear outer edge of shell 12 are aligned to the rear cut notches 31A and 30B of sling 14. The cut 43A and 43B of FIG. 3F are now joined to the cut notches 31A and 30A of the rear bumper again through stitch line 36. The stitch line 36 is preferably an overlock stitch that finishes the edge of the bumper as well as secures the bumper and sling together. Finally, elastic strip 13 is sewn to the rear bumper 12B, and the ends of the strip are secured and covered by loop-type filamentary material strips 26B, as shown in FIG. 3G.

Figure 4:
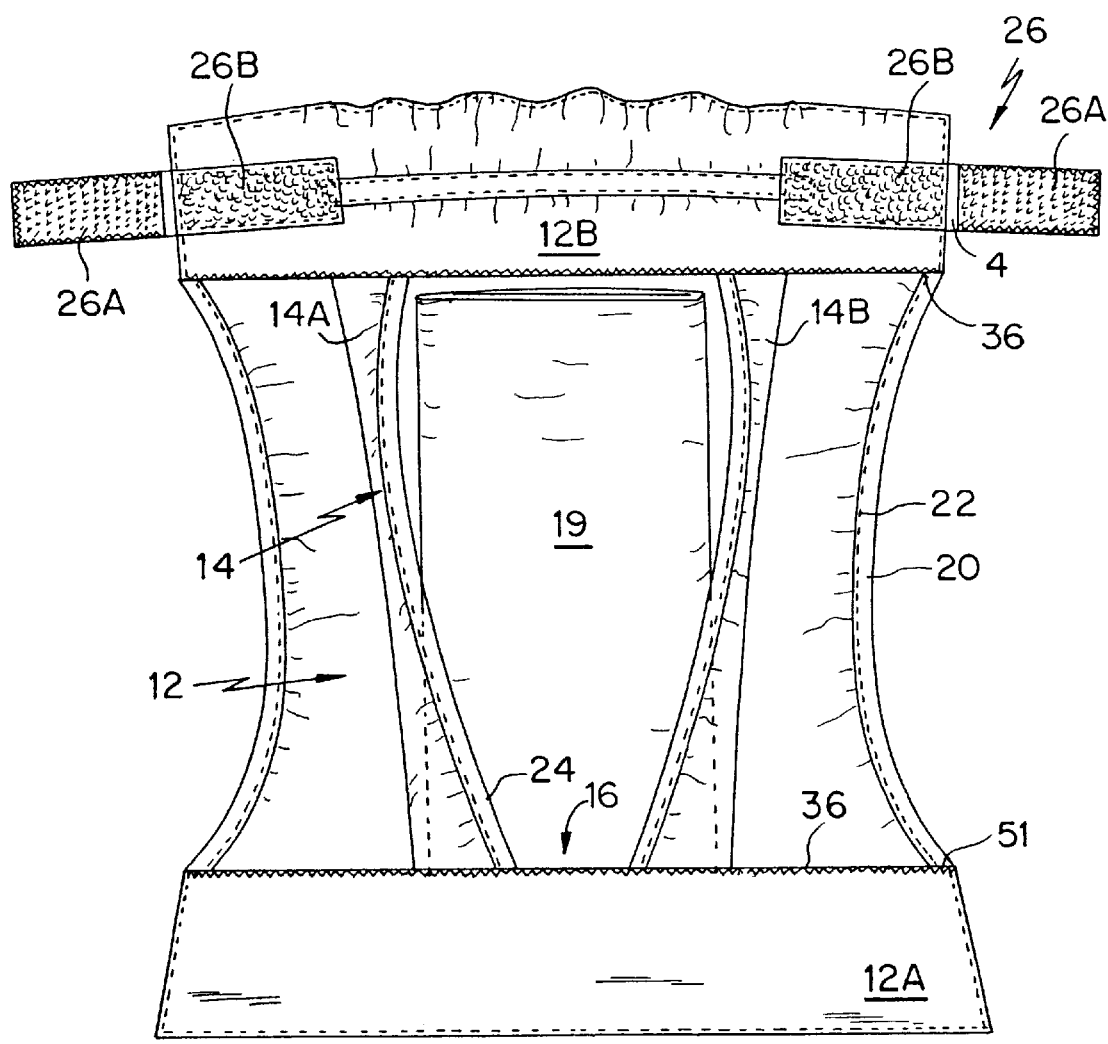
FIG. 4 is a plan view, with portions deleted for clarity, of a diaper having a tapered or trapezoidal sling in accordance with another embodiment of the invention.

FIG. 4 depicts another embodiment of the invention, modified only in that the sides 14A and 14B of sling 14 are folded inwardly at the frontal bumper portion of the shell 12A by amount of folding greater than that at the rear bumper 122 to produce a tapered sling configuration. This enables a wider area for accommodating the buttocks of an infant. Attachment line of stitching 36 in the rear portion and attachment line of stitching 51 in the frontal portion remain the same as described; only the points of attachment have changed to accommodate the increased width in the buttocks region.

Figure 5:
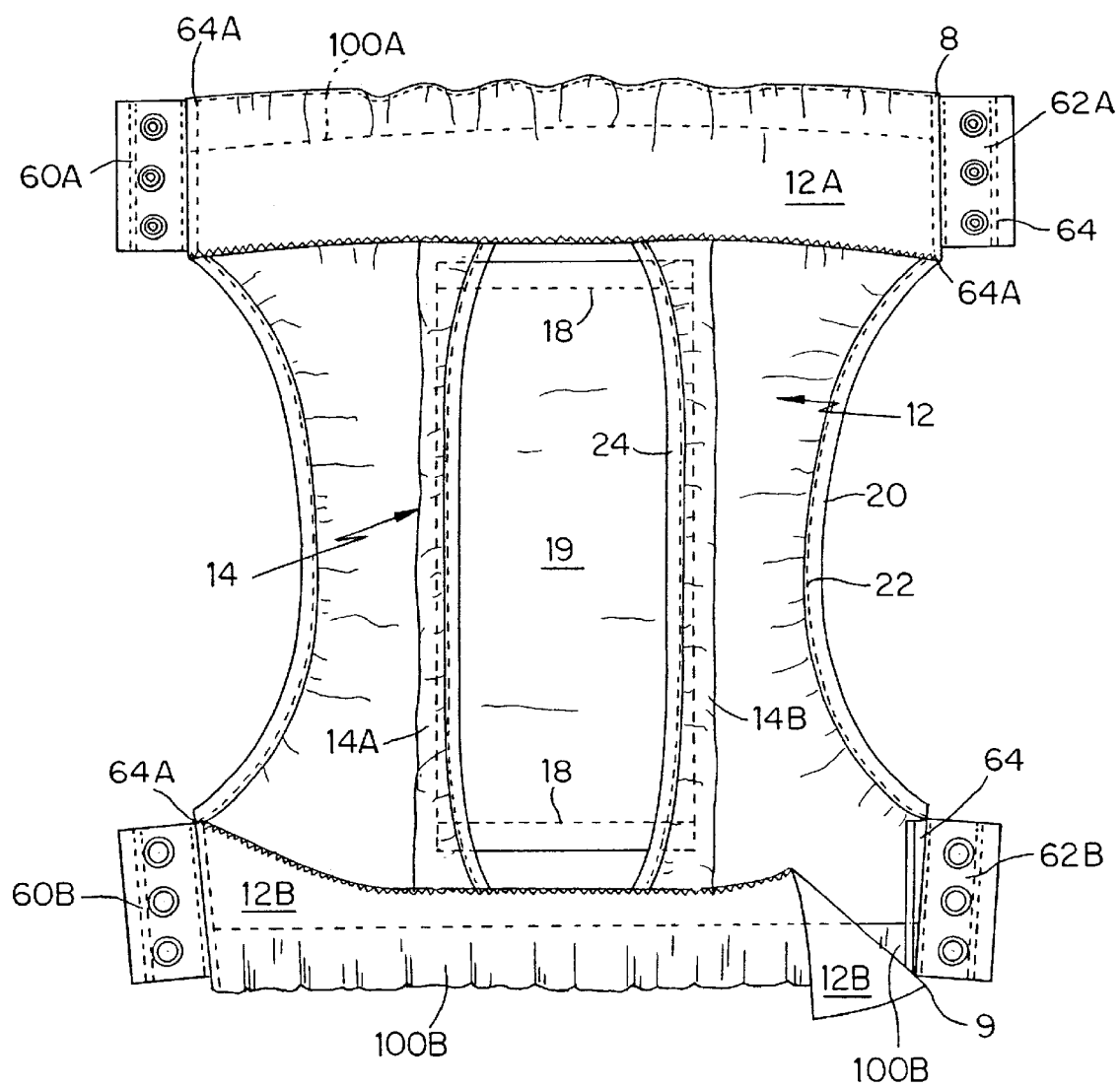
FIG. 5 is a plan view, with portions deleted for clarity, of a diaper of pull-up form and incorporating side snap fasteners in accordance with the invention.

In the embodiment of FIG. 5, filamentary tab fasteners 26 of bumper 12A and 50 of outer shell 12 are replaced by complementary snap fasteners 60A, 60B and 62A, 62B as fabric tabs extending from the frontal and rear bumpers 12A and 12B respectively. The frontal and rear bumpers 12A and 12B both retain an elastic strip 100A and 100B encased within folds 8 and 9 and gathering and proving a snug fit of the diaper to the waist of the infant. When snapped, the diaper of FIG. 5 may function as a pull-up training pant or diaper with pad 19 inserted or optionally sewn at 18. The remaining structure of the diaper or underwear is similar to that of the other embodiments. The tabs 60A, 60B, 62A and 62B are sewn and enclosed at 64 by folded fabric of shell 12 at fold lines 8 and 9. After the tabs are encased, they are top stitched at line 64A to further enhance their security.

Although the present invention has been described with reference to particular means, materials and embodiments, from the foregoing description one skilled in the art can easily ascertain the essential characteristics of the present invention, and various changes and modifications may be made to adapt the various uses and characteristics without departing from the spirit and scope of the present invention as described by the claims that follow.

What is claimed is:

1. A method of manufacturing a protective undergarment, comprising the steps of:

patterning one end of a generally rectangular piece of fluid resistant material to have a central projecting region adjoining sides demarked by a pair of notches cut into the material to form a sling;

backfolding the projecting region against said notches and folding in the sides of the sling;

securing the backfolded region of the sling to a frontal portion of a diaper shell;

folding the frontal portion of the shell, together with said backfolded sling region, onto an inner surface of the shell to form, at the same time, a shell frontal bumper and a hidden sling pocket;

stitching front ends of the sides of the sling and sides of the pocket to an undersurface of the frontal bumper while leaving a front end of the pocket open as the access opening to the pocket;

folding a rear portion of the shell to form a rear bumper; and stitching said rear bumper to a rear edge of the sling.

2. The method as in claim 1, including the steps of:

locating an attachment end of a filamentary fastener strip at each side of the rear portion of said shell, with the strip projecting outwardly from the shell; and wherein said step of rear portion folding comprises covering the attachment end of said strip with said rear bumper.

3. The method as in claim 2, further including:

locating a strip of elastic trim on said rear bumper; and covering exposed ends of said trim by complementary filamentary material.

4. A protective undergarment, comprising:

an outer shell formed of fluid resistant material and having frontal and rear ends folded in to an inner surface of said shell to form frontal and rear bumpers; and a sling formed of a fluid resistant material and having frontal and rear ends connected respectively to the frontal and rear bumpers, opposite sides of the frontal end of the sling being folded toward each other and connected to said frontal bumper, said frontal end of said sling having a central projecting portion extending beneath said frontal bumper, and said central projecting portion having three sides attached and a fourth side unattached to an inner surface of said frontal bumper for forming a hidden pocket with an opening at the unattached side of the central projecting portion to receive one end of a fluid absorbent pad.

5. The undergarment as in claim 4, including resilient material in said rear bumper for gathering at a waist of a wearer.

6. The undergarment as in claim 4, including filamentary fastener strips extending from said rear bumper, and a complementary filamentary fastener strip on an outer surface of said shell for coupling to said fastener strips when the undergarment is worn.

7. The undergarment as in claim 4, including a fluid absorbent pad retained in said sling.

8. The undergarment as in claim 4, wherein the sling, when folded, is approximately rectangular.

9. The undergarment as in claim 4, wherein opposite sides of said sling attached to said shell are spaced apart from each other by a distance slightly greater at said rear bumper than at said frontal bumper.

10. The undergarment as in claim 4, including elastic trim on oppsite sides of said outer shell between said frontal and rear bumpers.

11. The undergarment as in claim 4, including elastic trim on exposed edges of sides of said sling.

12. A protective undergarment, comprising:

an outer shell formed of fluid resistant material;

frontal and rear end portions of the outer shell folded to an inner surface of the outer shell to form frontal and rear connecting pieces of fluid resistant material; and a sling formed of a rectangular piece of fluid resistant material having a central projecting portion of material demarked by a pair of notches cut into the sling defining opposite sides of said sling which fold laterally inward and attach to said one of said frontal and rear connecting pieces, the central projecting piece having three sides attached and a fourth side unattached to an inner surface of said one of said frontal and rear connecting pieces and forming a hidden pocket with an opening at the unattached side of the central projecting piece to receive one end of a fluid absorbent pad.

13. The undergarment as in claim 12, including filamentary fastener strips extending from said rear connecting piece, and a complementary filamentary fastener strip on the outer surface of said shell for coupling to said fastener strips when the undergarment is worn.

14. The undergarment as in claim 12, including a fluid absorbent pad retained in said sling.

15. The undergarment as in claim 12, wherein said sling is wider at said rear connecting piece than at said frontal connecting piece.

16. The undergarment as in claim 12, including elastic trim on opposite side edges of said outer shell between said frontal and rear connecting pieces of said outer shell.

17. The undergarment as in claim 12, including elastic trim on exposed opposite side edges of said sling.

* * * * *